United States Patent [19]

Bertholet et al.

[11] Patent Number: 5,779,707
[45] Date of Patent: Jul. 14, 1998

[54] LINK PIECE FOR BONY ELEMENTS

[76] Inventors: Maurice Bertholet, La Rochette, Les Cotes, F-38360 Sassenage; Philippe Morilleau, 20, Bd Jean Pain, F-38000 Grenoble, both of France

[21] Appl. No.: 538,345

[22] Filed: Oct. 3, 1995

Related U.S. Application Data

[63] Continuation of Ser. No. 151,028, Nov. 12, 1993, abandoned.

[30] Foreign Application Priority Data

Nov. 13, 1992 [FR] France ................... 92 13802

[51] Int. Cl.⁶ ........................................ A61B 17/68
[52] U.S. Cl. ........................ 606/75; 606/72; 606/78
[58] Field of Search ........................ 606/61, 72, 73, 606/75, 76, 78, 105, 69, 60, 215, 216, 219, 220

[56] References Cited

U.S. PATENT DOCUMENTS

| | | | |
|---|---|---|---|
| 4,170,990 | 10/1979 | Baumgart et al. | 606/75 |
| 4,444,181 | 4/1984 | Wevers et al. | 606/75 |
| 4,485,816 | 12/1984 | Krumme | 606/219 |
| 4,887,601 | 12/1989 | Richards | 606/219 |
| 4,913,144 | 4/1990 | Del Medico | 606/75 |
| 5,246,443 | 9/1993 | Mai | 606/78 |
| 5,314,427 | 5/1994 | Goble et al. | 606/72 |

FOREIGN PATENT DOCUMENTS

| | | | |
|---|---|---|---|
| 850067 | 7/1981 | U.S.S.R. | 606/78 |
| 1152582 | 4/1985 | U.S.S.R. | 606/78 |
| 1405829 | 6/1988 | U.S.S.R. | 606/75 |
| 1657173 | 6/1991 | U.S.S.R. | 606/72 |
| 1671275 | 8/1991 | U.S.S.R. | 606/75 |

*Primary Examiner*—Guy V. Tucker
*Attorney, Agent, or Firm*—Michael D. Bednarek; Kilpatrick Stockton LLP

[57] ABSTRACT

A link piece for bony elements comprises a central portion and at least two anchoring portions rigidly connected to the central portion. The central portion is made of a shape memory effect material and the central portion comprises a central hole, whereby a shape variation of this central portion causes a variation of the distance between the at least two anchoring portions while these at least two anchoring portions move from each other along a straight line.

10 Claims, 4 Drawing Sheets

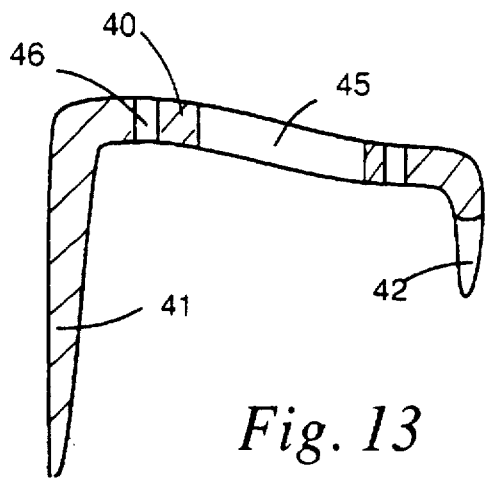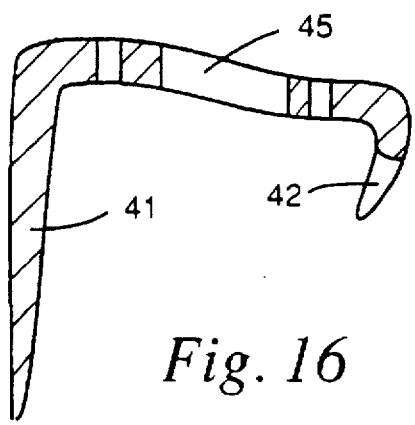
Fig. 13    Fig. 16
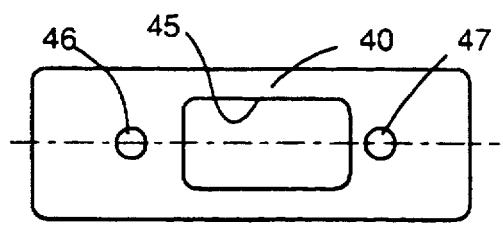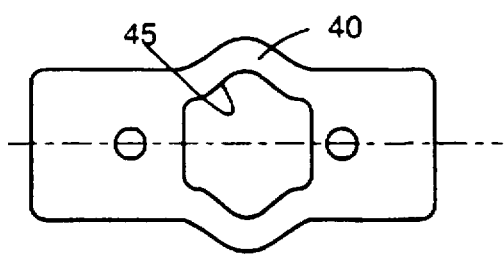
Fig. 15    Fig. 17
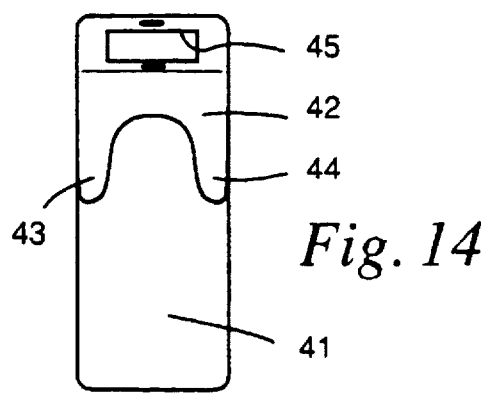
Fig. 14
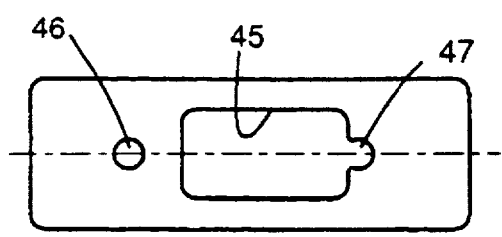
Fig. 18

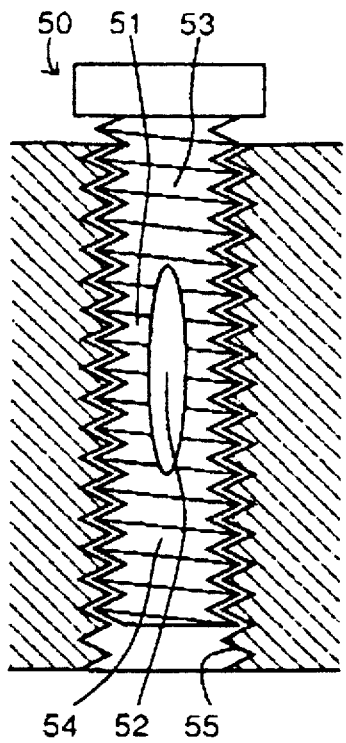
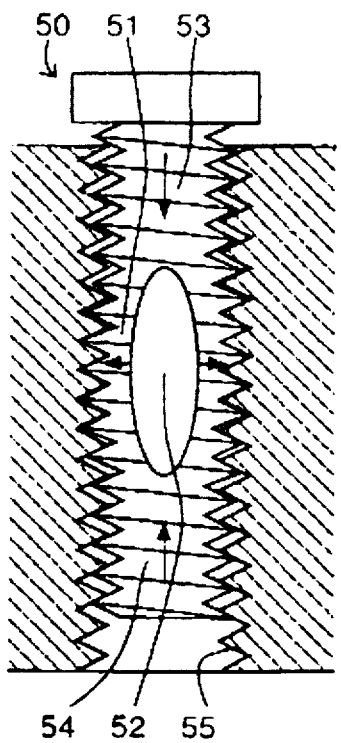
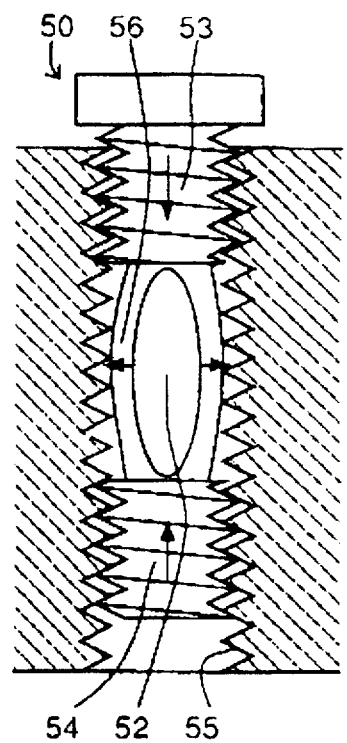
*Fig. 19*   *Fig. 20*   *Fig. 21*
*Fig. 22*   PRIOR ART
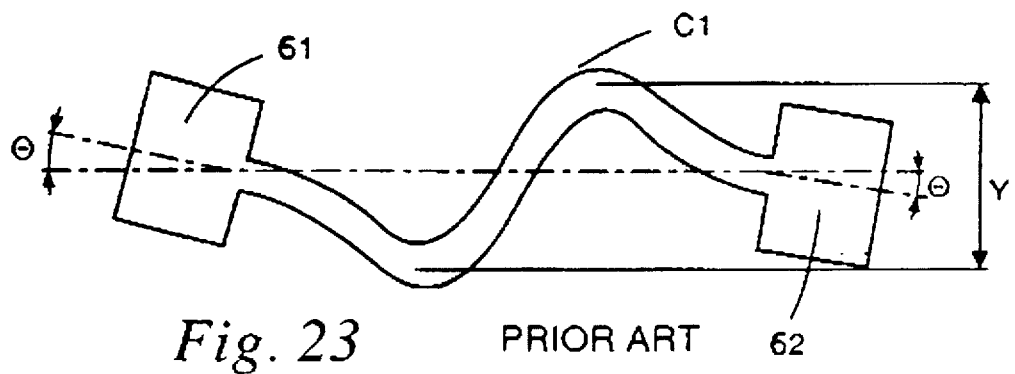
*Fig. 23*   PRIOR ART

LINK PIECE FOR BONY ELEMENTS

This application is a continuation of application Ser. No. 08/151,028 filed Nov. 12, 1993, now abandoned.

BACKGROUND OF THE INVENTION

The present invention generally relates to link pieces for bony elements, which generally comprise a central portion and at least two anchoring portions located substantially near ends of the central portion.

Many link pieces for linking or joining together bony elements, for bony reconstitution or soldering therebetween, are known.

Surgical staples or plates for holding or connecting bones or soft tissues are well known. At least a portion of the staple or plate material is made of a shape memory effect material (also referred SME material). A shape memory effect material is a material the shape of which changes when its temperature changes from a temperature lower than the martensitic transformation temperature to a temperature higher than the austenitic transformation temperature.

Staples or osteosynthesis plates made of a thermoelastic and martensitic alloy are also known. Such staple or plate is "educated", i. e., plastically distorted, for offering a straight shape (see FIG. 22 illustrating prior art) at a temperature lower than the martensitic transformation temperature of the material, and thereafter a waved shape (see FIG. 23 illustrating prior art) inducing a shortening of its length is obtained as its temperature become higher than the austenitic transformation temperature of said material.

A drawback of these prior art techniques is that a shortening of the plate length is obtained by increasing bendings of the waved shape. Thus, in this case, the two opposite plate ends rotate each other while they approach each other, as it can be seen by rotation θ on FIG. 23 illustrating prior art, i. e., these ends do not keep parallel directions. It results that the anchoring portions located at the opposite ends of the waved portion cannot be efficiently fixed in the corresponding bony element because they rotate (see rotation θ) during their approaching movement. Under these conditions, the osteosynthesis phenomenon cannot be efficiently provided, for example, because two separate bony elements which are so linked to each other through a staple or a plate are well brought closer together but do not stay accurately aligned to each other.

FIG. 22 and 23 schematically illustrate a prior art staple having a waved portion 50, the staple being shown in an expanded position and in a retracted position for showing the harmful phenomenon of rotation θ of the ends 61 and 62 upon the retraction movement, respectively. In other words, during a retracting movement of the staple, its ends cannot keep their parallel position each other.

With prior art staples, the central portion of the staple is relatively narrow and cannot provide a lateral stability of the staple. If the central portion is wider, its weight or cost is increased. In view to increase the lateral stability, it is desirable to associate with such a staple lateral connection elements for fixing the central portion of the staple on a lateral bony portion in.

On the other hand, with the prior art staples, the force of the anchoring portions is relatively low for a given section of the waved central portion of the staple.

It is an object of the present invention to provide such a link piece for linking bony elements comprising a central portion and at least two anchoring portions rigidly connected to the central portion in which the anchoring portions can move away and near from each other without any rotation of said anchoring portions during their said movement.

It is another object of the present invention to provide such a link piece in which the away or near force of the anchoring portions is relatively high for a given section of the central portion.

It is another object of the present invention to provide such a link piece which is able to associate to it elements for providing its lateral stability.

SUMMARY OF THE INVENTION

According to a main feature of the invention, a link piece for bony elements comprising a central portion and at least two anchoring portions rigidly connected to the central portion is characterized in that the central portion is made of a shape memory effect material and in that the central portion comprises a central hole, whereby a shape variation of this central portion causes a variation of the distance between said at least two anchoring portions while these at least two anchoring portions move from each other along a straight line.

According to a preferred embodiment of the invention, said central portion is of a generally circular or oval shape.

According to another embodiment of the invention, said central portion is of a generally disc shape with a slot in its central portion.

BRIEF DESCRIPTION OF THE DRAWINGS

The above-mentioned together with other objets, features and advantages of the present invention will become apparent from the following detailed description of embodiments, with reference being made to the following drawings.

FIG. 13 is a longitudinal cross-section view of yet another embodiment of a link piece according to the present invention, this link piece constituting a "knee plate" according to the present invention being in an expanded position:

FIG. 14 is a side view of the piece of FIG. 13;

FIG. 15 is a top view of the piece of FIG. 13;

FIG. 16 is a view similar to that of FIG. 13 but in which the piece is in a retracted position;

FIG. 17 is a top view of the piece of FIG. 16 when in a retracted position;

FIG. 18 is a top view of an alternative embodiment of the piece illustrated in FIG. 13 to 17;

FIG. 19 is a side view of another embodiment of a link piece according to the present invention;

FIG. 20 is a view similar to that o FIG. 19 but in which the piece is in a retracted position;

FIG. 21 is a side view of another embodiment of a link piece according to the present invention; and FIG. 22 and 23 are bottom views of a retractable staple by means of a deformation of a central portion of a shape memory material, this staple being known from the prior art and illustrated when in an expanded position in FIG. 22 and when in a retracted position in FIG. 23, those two drawings having been previously commented on.

DESCRIPTION OF THE PREFERRED EMBODIMENTS

Figure 1:
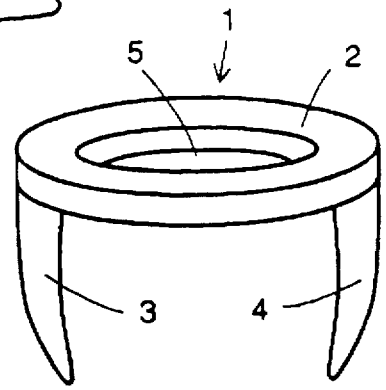
FIG. 1 is a perspective view of an embodiment of a link piece according to the present invention.

In FIG. 1, a link piece for bony elements 1 according to the invention comprises a central portion 2 and at least two anchoring portions 3, 4 rigidly connected to central portion 2. The anchoring portions 3, 4 can be rigidly connected to the central portion 2 for example by screwing, soldering, or anchoring portions 3, 4 can be made integrally with central portion 2.

The central portion 2 comprises a central hole 5. In other words, the central portion is of a generally ring-like shape. It can be also said that central portion 2 has a generally "buttonhole" shape. The main characteristics of central portion 2 is that the central hole 5 is entirely surrounded by a material, i.e. it is not laterally open.

Figure 2:
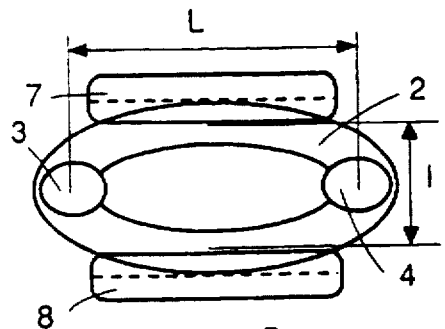
FIG. 2 is a bottom view of the link piece of FIG. 1 when it is in an expanded position which is obtained by means of a tool which is illustrated.
Figure 4:
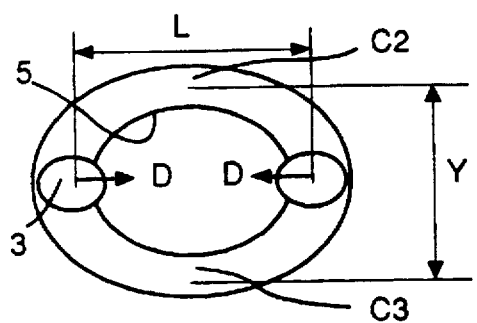
FIG. 4 is a bottom view of the link piece of FIG. 2 when it is in a retracted position.

In FIG. 1, the central hole 5 is of a generally oval shape, as can be also seen in FIG. 2 and 4. However, other shapes of central hole 5 can be provided. For example, in FIG. 6, the central hole has an elongated slit shape 6.

Referring again to FIG. 1–4, the central portion 2 of link piece 1 forms a ring which substantially lies in a plane (not shown, but this plane is the plane of the sheet for FIG. 2 and 4). The anchoring portions 3, 4, in this example, are constituted by tapered extensions which are relatively elongated, which extensions extend substantially perpendicularly to the plane in which the central portion 2 lies. These anchoring portions 3, 4 can have any other shape as desired. For example, the anchoring portions can outwardly extend, substantially in the same plane as the plane of the central portion 2 and can comprise at their respective ends holes or windows for passing through anchoring screws (not shown). In the following description, any rigid element or piece for providing a rigid anchoring or linkage with an bony element is referred as "anchoring portion" whatever the shape of this piece or element is.

In FIG. 2, the link piece 1 is in an expanded position, i.e. a position in which the anchoring portions are substantially far from each other. This expanded position can be obtained because the central portion 2 of the link piece is made of a shape memory effect material. A shape memory material is a material which can be "educated" (i.e. plastically deformed) so that it presents a given geometric shape at a temperature lower than the martensitic transformation temperature and another different geometric shape at a temperature higher than the austenitic trnsformation temperature.

Many materials which are "shape memory effect materials" are well known. A great number of these materials with shape memory effect can be used in surgery provided that these materials are physiologically compatible. Generally, shape memory effect materials based on titanium are provided.

Figure 3:
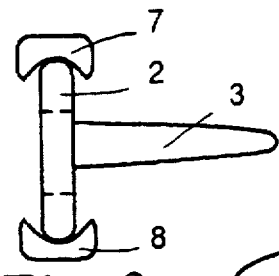
FIG. 3 is a side view of the link piece of FIG. 2.

The link piece 1 which is in its expanded position, as illustrated in FIG. 2, is brought into this expanded position by cooling the piece, for example by bringing it at a temperature lower than 10° C. and by nipping the link piece by means of an appropriate nipper the ends of which cooperating with the link piece are illustrated in FIG. 2 and 3 by means of reference index 7 and 8. In FIG. 2 and 3, the ends 7, 8 of the nipper can be of an elongated shape with a longitudinal groove 9, 10 in which is seated the corresponding lateral edge of the central portion 2 of the link piece. When the link piece 1 is so brought in this expanded position, the central portion 2 takes an elongated shape, i.e. a generally oval shape with a substantially narrow width. When the link piece has so been brought in its expanded position, it can be released from the nipper 7, 8 and it can be set so that its anchoring portions are fitted into corresponding holes or portions of bony elements (not shown). After that, the heat of the human body quickly warm up the link piece 1 and brings it to the body temperature, i.e. a temperature substantially higher than the austenitic transformation temperature of the piece. Under this condition, the shape memory effect material constituting the central portion 2 of the link piece resumes its initial shape corresponding to the shape illustrated in FIG. 4. In FIG. 4, the link piece has so resumed a retracted position for which the central portion 2 takes an oval shape the width of which is substantially greater than the width l that the central portion took when it was in the expanded position (FIG. 2) and the length of which L is shortened. In this "retracted position", the central portion 2 approaches to a substantially circular shape and therefore, the anchoring portions 3, 4 are brought near each other. The central portion 2 has a symetric shape relative to a line 11 connecting the two anchoring portions 3, 4. This results in that the movement vectors D of the anchoring portions 3 and 4 are along this line 11, i.e. these two movement vectors D are aligned or parrallel each other.

When the link piece warms up after it has been located on the human body, the anchoring portions 3 and 4 of the link portions 3 and 4 of the link piece are brought nearer each other, so providing a relative translation movement that is free of any associated rotation or pivot movement. This is particularly interesting for the purpose of causing a relative movement of two separate bony elements for the purpose of bringing them together without causing a rotation or a pivot movement. This provides both an excellent relative positioning of the bony elements that should be associated and a correct maintaining of the anchoring portions inside the corresponding bony elements because these anchoring portions 3, 4 do not pivot relative to each other when they move.

A lot of tests have made by the inventor and have shown that such a link piece such as that illustrated in FIG. 1 to 5 is able to provide a movement of the anchoring portions 3, 4 relative to each other without the anchoring portions angularly displaced from each other by more than one degree in any direction of space.

When one utilizes link pieces for linking bony elements, it is desired that all the portions of the link piece are made with a substantially constant cross-section value. In other words, it is desired that a link piece for linking bony elements will not have, in some locations of the piece, a metallic mass very high and in other locations of the piece a metallic mass very low. This can be provided with the link piece according to the present invention because of the ring or buttonhole shape of the central part 2 of the piece.

Otherwise, this ring or buttonhole shape of the central portion 2 of the link piece provides a force for moving each other the anchoring portions 3 and 4 is relatively important for a given cross-section value of the central portion 2. One can understand this phenomenon by referring to FIG. 3 and to prior art FIG. 23. In the prior art, one can see that with a given width Y of the central portion and a given flectional moment M (i.e. with a given cross-section) of the central portion C1 of the piece, the contraction force F1 of the piece is as follows:

$$F1=M.Y$$

On the other hand, for the piece according to the invention (FIG. 3), with the same width Y and the same flectional moment M of each of the lateral portions C2 and C3, the contraction force F2 of the piece is as follows:

$$F2=2 M.Y$$

Consequently, F2=2×F1

Moreover, one can see that, for a relatively light metallic mass, the central portion 2 of the link piece has a substantially wide and planar symetrical shape that can be satisfactory applied against a lateral top surface of the bony elements, which provides a good transversal or lateral stability of the link piece. Besides, it is possible to associate to the lateral portions of the central piece 2 elements (not shown) for fixing these lateral portions to the bony elements for increasing the lateral stability of the link piece. This is rendered possible because the central portion 2 has a ring shape.

Figure 6:
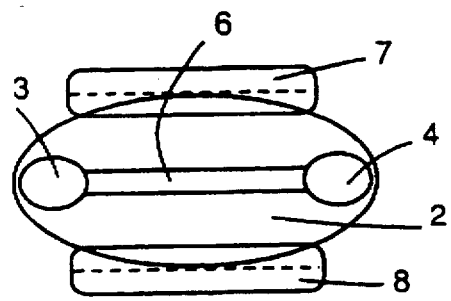
FIG. 6 is a bottom view of the link piece of FIG. 5 when it is in an expanded position.
Figure 5:
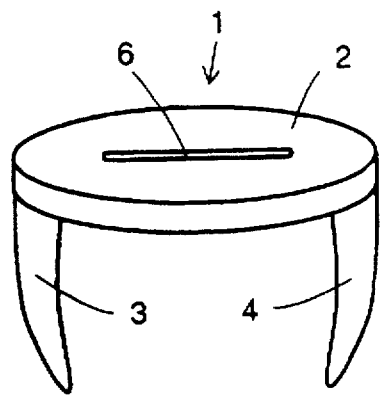
FIG. 5 is a perspective view of another embodiment of a link piece according to the present invention.
Figure 7:
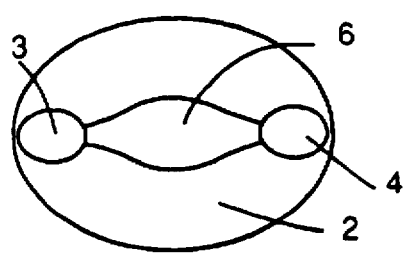
FIG. 7 is a bottom view of the link piece of FIG. 6 when it is in a retracted position.

In FIG. 6 and 7, a top view of the alternative embodiment of the link piece illustrated in FIG. 5 is shown. In FIG. 6, the link piece of FIG. 5 is illustrated in its expanded shape and in FIG. 7, the same link piece is illustrated in its retracted shape. The operation mode of the link piece illustrated in FIG. 5 to 7 is exactly the same as that of the link piece illustrated in FIG. 1 to 4, the difference concerning only the shape of the central hole which is a slit 6.

Figure 8:
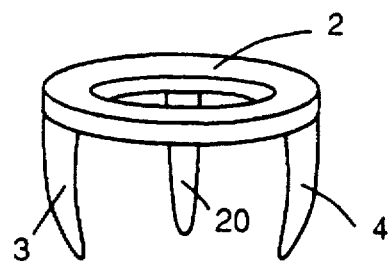
FIG. 8 is a perspective view of another embodiment of a link piece according to the present invention.

In FIG. 8, an alternative embodiment of a link piece according to the invention in which the ring central portion 2 comprises two anchoring portions 3, 4 but also an additional lateral anchoring portion 23 connected to one of the sides of the central portion 2 is illustrated.

Figure 9:
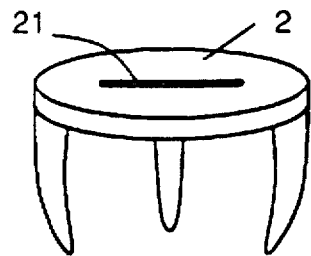
FIG. 9 is a perspective view of yet another embodiment of a link piece according to the present invention.

In FIG. 9, a link piece which is wholly similar to the one in FIG. 8 but in which the central hole of the central portion 2 is of a slot shape 21 is illustrated. One can intend too a link piece similar to the one in FIG. 8 or FIG. 9 but in which four anchoring portions symetrically located to each other, i.e. located at the four corners of a square or a rectangle could be provided. In this case (not shown), two anchoring portions are located on one end (in the place of the anchoring portion 3 of FIG. 1) and two other anchoring portions are located symetrically on the other end (in the place of the anchoring portion 4 of FIG. 1), and these two pairs of anchoring portions move away or near from each other in a parallel manner, i.e without pivoting one to each other.

Figure 10:
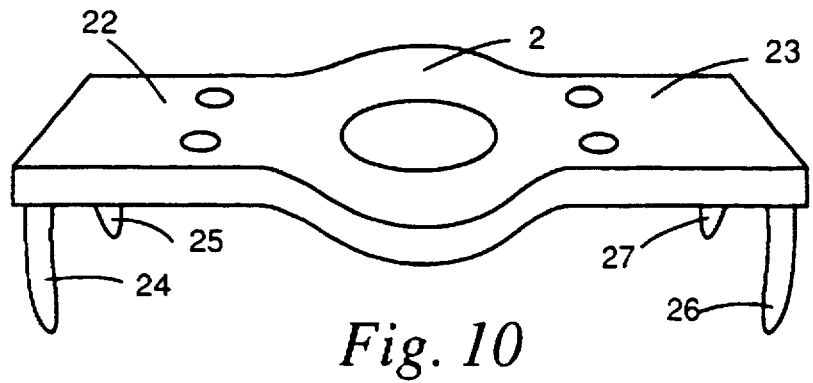
FIG. 10 is a perspective view of yet another embodiment of a link piece according to the present invention.

In FIG. 10, an alternative embodiment of a link piece according to the invention in which the central portion 2 is longitudinally extended by anchoring portions forming first a plate shaped portion 22, 23 at the end of which two symetrical anchoring portions 24, 25 and two symetrical anchoring portions 26, 27 are fixed is illustrated.

Figure 11:
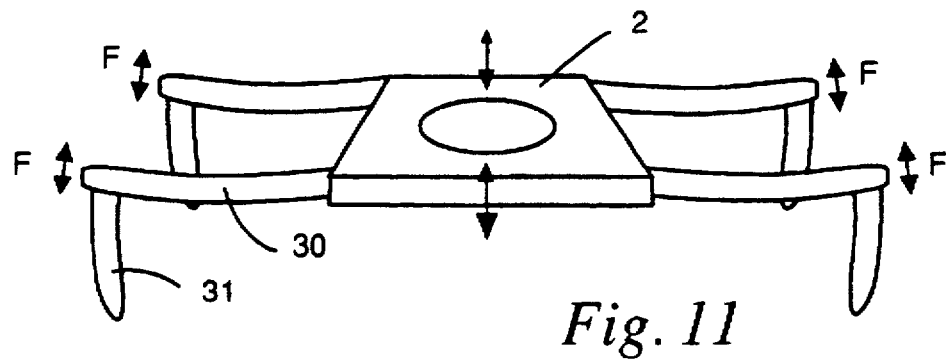
FIG. 11 is a perspective view of yet another embodiment of a link piece according to the present invention.

In FIG. 11, an alternative embodiment of the link piece in FIG. 10 is illustrated and in this alternative embodiment, the central portion 2 is of an substantially square or rectangular outer shape from which anchoring portions outwardly extend, a first portion 30 of which outwardly extends, substantially in the plane of the central portion 2 and a second portion 31 of which extends substantially perpendicularly to the plane of the central portion 2. One can so constitute four symetrical anchoring portions, i.e. located substantially at the four corners of a square or rectangle.

Figure 12:
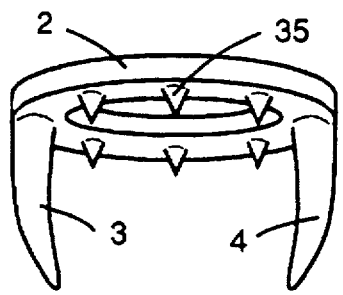
FIG. 12 is a perspective view, slightly from the bottom, of yet another embodiment of a link piece according to the present invention.

In FIG. 12, another alternative embodiment of a link piece according to the invention is illustrated, in which secondary anchoring elements 35 having a nail shape or a tapered protrusion shape are located beneath the central portion 2 of a ring shape to come in close contact with lateral outer portions of the bony elements anchored on the link piece.

In FIG. 13–18, another possible application of the invention is illustrated, this application concerning that is called a "knee plate" which is a piece for fixing tibia osteotomies. In FIG. 13, one can see a "knee plate", in a longitudinal section. In FIG. 14, one can see this same piece in a side view and in FIG. 15, one can see this same piece in a top view. The "knee plate" is constituted by a central portion 40 which is substantially plane, an elongated anchoring portion 41 sometimes referred as "anchoring plate" or "plate", which extends substantially perpendicularly to the central portion 40, and a short anchoring portion havo,g a hook shape 42 which extends substantially perpendicularly to the central portion 40. The anchoring plate 41 is substantially straight and has an elongated rectangular shape and the anchoring portion 42 is inwardly bent and has a reverse U shape, i.e. it comprises two lateral hooks 43, 44. As one can see mainly on FIG. 15, the central portion 40 comprises a central hole 45 that can be round, square or rectangular. In its extended condition, the central hole can be, for example, has a generally substantially rectangular shape, as illustrated in FIG. 15 and in its retracted position, the central portion 40 which is made of a shape memory effect material can laterally extend, as illustrated in FIG. 17, whereby the two opposed anchoring portions 41 and 42 are brought near together, so providing an axial compression. Eventually, the central portion 40 comprises moreover small diameter holes 46, 47 that permit to screw the piece on a bony element, particularly a bone of the knee. One can foresee too to make the portion 42 of a shape memory material so that this portion inwardly bends when the central portion 40 contracts, as one can see by comparing FIG. 13 (expanded position) and FIG. 16 (retracted position).

According to an alternative embodiment illustrated in FIG. 18, the hole 47 which is situated on the side of the short anchoring portion 42 can open into the central hole 45 so that it increases substantially the size of the central hole 45.

Refering now to FIG. 19–21 it is also possible to apply the invention to a fixing rod or screw, sometimes referred as a "medullar nail" or "medullar screw" or "surgical screw" or "dental implant". In this case, the rod or screw 50 is of a substantially constant section along its length and comprises a central portion 51 with one or more slots or holes 52 passing through it. Two end areas 53, 54 of the screw are threaded and constitute the above described "anchoring portions". The central hole 52 acts for contracting the screw along its length and eventually for imparting a lateral thrust on the inner walls of a hole inner threaded 55 of the bone through which the screw is fitted. In FIG. 21, the central outer portion 56 is restricted and does not include threads.

The invention is not restricted to the above described embodiments but the invention will be applied to all conceivable modifications being in the general scope and spirit of the invention.

We claim:

1. A link piece for bony elements comprising:
   a planar central portion made from a shape memory effect material and including a central hole formed therethrough; and
   at least two anchoring portions connected to said central portion and extending substantially perpendicular to the plane in which said central portion lies wherein a distance between said at least two anchoring portions is variable along a straight line in correspondence with a variation in a shape of said central portion, said variation in distance being substantially free from angular displacement of said at least two anchoring portions relative to said central portion.

2. A link piece according to claim 1, wherein said central portion has one of a generally circular shape and a generally oval shape.

3. A link piece according to claim 1, wherein said central portion is generally disc-shaped and said central hole is generally slot-shaped.

4. A link piece according to claim 1, wherein said shape memory effect material is titanium based.

5. A link piece for bony elements comprising:
   a planar central portion, said central portion being made of a shape memory effect material and being provided with a central hole; and
   a plurality of anchoring portions rigidly connected to said central portion and extending from said central portion in the direction substantially perpendicular to a plane in which said central portion lies, said central hole extending from one of said anchoring portions to another one of said anchoring portions, wherein a distance between respective ones of said plurality of anchoring portions is variable along a straight line in correspondence with a variation in a shape of said central portion, said variation in distance being substantially free from angular displacement between said anchoring portions and said central portion.

6. A link piece according to claim 5, wherein said central portion has one of a generally circular shape and a generally oval shape.

7. A link piece according to claim 5, wherein said central portion is generally disc-shaped and said central hole is a slot.

8. A link piece according to claim 5, wherein said shape memory effect material is titanium based.

9. A link piece for bony elements comprising:
   a planar central portion made from a shape memory effect material and having a hole formed therethrough;
   a plurality of members connected to said central portion and extending therefrom substantially in the plane in which said central portion lies; and
   a plurality of anchoring members connected to respective distal ends of said plurality of members, with respect to said central portion, said plurality of anchoring members extending in a direction substantially perpendicular to said plane in which said central portion lies, wherein a distance between respective ones of said plurality of anchoring members is variable along a line in correspondence with a variation in a shape of said central portion, wherein said variation in distance between said anchoring portions is substantially free of angular displacement of said anchoring portions relative to said corresponding members to which said anchoring portions are connected.

10. A link piece according to claim 9, wherein said shape memory effect material is titanium based.

* * * * *